United States Patent
Lo et al.

(10) Patent No.: US 7,901,712 B2
(45) Date of Patent: Mar. 8, 2011

(54) GLICLAZIDE NANOSPHERE AND MANUFACTURING METHOD THEREFOR AND APPLICATION THEREOF

(75) Inventors: Yung-Kuang Lo, Kaohsiung (TW); Thau-Ming Cham, Kaohsiung (TW)

(73) Assignee: Kaoshiung Medical University, Kaohsiung (TW)

( * ) Notice: Subject to any disclaimer, the term of this patent is extended or adjusted under 35 U.S.C. 154(b) by 1153 days.

(21) Appl. No.: 11/595,250

(22) Filed: Nov. 10, 2006

(65) Prior Publication Data

US 2008/0075783 A1    Mar. 27, 2008

(51) Int. Cl.
*A61K 9/50*    (2006.01)
(52) U.S. Cl. .............................. 424/490; 264/5; 977/906
(58) Field of Classification Search .................... 424/490
See application file for complete search history.

(56) References Cited

U.S. PATENT DOCUMENTS

2006/0002998 A1    1/2006    Trehan et al.

OTHER PUBLICATIONS

Ozkan et al (Improvement of water solubility and in vitro dissolution rate of gliclazide by complexation with beta-cyclodextrin.Pharm Acta Helv. Apr. 2000;74(4):365-70).*

* cited by examiner

*Primary Examiner* — Jake M. Vu
(74) *Attorney, Agent, or Firm* — Volpe and Koenig P.C.

(57) ABSTRACT

An novel gliclazide nanosphere, the manufacturing method therefor and the application thereof are provided in the present application is provided. The gliclazide nanosphere is prepared by reacting the solid gliclazide with a polymeric matrix for improving the dissolution property and safety of gliclazide, and is benefit for immediately releasing dosage application in clinical therapy.

9 Claims, 4 Drawing Sheets

GLICLAZIDE NANOSPHERE AND MANUFACTURING METHOD THEREFOR AND APPLICATION THEREOF

FIELD OF THE INVENTION

The present invention relates to a gliclazide nanosphere, and more particularly to a gliclazide nanosphere with an average particle size ranged from 56.30 nm to 60.46 nm for improving the dissolution property and safety thereof.

BACKGROUND OF THE INVENTION

The cyclodextrins, CDs, as know as the cyclic oligosaccharides, have six to eight glucose unites linked by the α-1, 4-glucosidic bonds, where CDs are usually nonhygroscopic and crystalline materials. The molecule of CDs is also distinguished for having a cylinder-shape, a macro ring structure and a large internal axial cavity. Contrary to the character of hydrophobic on the internal cavity of CDs, the outer surface thereof is hydrophilic. It is found that CDs are able to form the inclusion complexes with many drugs due to the possession of its cavity by either the whole or partial drug molecule. With the aim of improving pharmaceutical interest, such as the solubility in aqueous media, the dissolution rate, the chemical stability and the bioavailability, the application of complexation in different drugs with CDs has been extensively studied in the recent years.

Although the inclusion complex made with CDs can improve the dissolution rate of many insoluble drugs, the safety aspects of CDs for the various routes of administration are not yet completely clarified. Several issues are discussed as following: for cellular interactions, CDs could induce shape changes of cellular membrane invagination on the human erythrocytes and even cause lysis under a high concentration rate of CDs. As to the parenteral safety issue, it is found that CDs could induce the nephrotoxicity and some hepatic disorders. Due to lacking of absorption through the gastrointestinal tract, all toxicity studies of orally administered CDs were shown as practically nontoxic. Nevertheless, the inhibition of mammalian amylases by β-CD potentially turns the digestible starches into materials that can not be digested and causes an increased incidence of soft stools and diarrhea. In the ophthalmic use of CDs, the increase in solubility and/or stability could avoid the irritation and discomfort of drug; however, high concentration of CDs could have an opposite effect of irritating the conjunctival and corneal surface and causing the reflex tearing and blinking. Some reports indicated that nasal preparation with CDs could cause the hemolytic activity of the nasal mucous membrane or ciliotoxicity. When using CDs as rectal absorption enhancers, the irritating effects of CDs on the rectal mucosa and the potential for systemic absorption of the pathogenic substances need to be considered, because it might cause severe irritation with erosion of the rectal mucosa. Finally, CDs may have some interactions with some components of the skin, which may reduce the function of skin as a barrier and contribute in part to the enhancement of drug absorption.

Nanospheres are solid colloidal particles with the size thereof being range between 10 to 1000 nm that have been employed to ameliorate the solubility and the dissolution rates for the water insoluble drugs. It has known that reducing the size of drug particle can increase its particle surface area, and can also improve its solubility and dissolution rate. Different techniques have been used to manufacture nanosized drug particles, such as dry and wet milling and solvent-based techniques, such as the emulsification-solvent evaporation, the emulsification-solvent diffusion and the precipitation solvent evaporation. As one of new alternative device for drug manufacturing, nanospheres have been used for parenteral injection and oral administration. For clinical application, nanospheres are reported being not only to increase the therapeutic efficiency of drug but also to reduce the quantity of drug administrated and to minimize undesirable side effects.

Gliclazide, 1-(1-azabicyclo(3,3,0)octyl)-3-(p-tolylsulfonylurea), which is termed GL hereafter, as a second generation sulfonylurea, is widely used in the treatment of non-insulin dependent diabetes mellitus (NIDDM). Because of its short-term acting, GL has been considered suitable for diabetic patients with renal impairment and for elderly patients that have reduced renal function and follow a sulphonylureas treatment which may increase the risk of hypoglycemia. The molecule of GL or the GL solid complex represent the following characters as low solubility in gastric fluids, low dissolution rate and inter-individual variability in its bioavailability.

Based on the above, to develop a new GL nanosphere and a manufacturing method therefor has become a major subject in this art, wherein the GL nanosphere not only increases the solubility and dissolution rate for GL, but also takes considerations to the various dosage forms for GL.

In order to overcome the drawbacks of the GLs or the GL solid complexes in the prior art, the novel GL nanosphere with increased solubility, enhanced dissolution rate, safety, and being free from the undesirable side effects derived from the carrier or excipient, the manufacturing method therefor and the application thereof are provided. The particular design in the present invention not only solves the problems described above, but also is easy to be implemented. Thus, the invention has the utility for the industry.

SUMMARY OF THE INVENTION

In accordance with one aspect of the present invention, a manufacturing method for a gliclazide nanosphere is provided. The manufacturing method includes steps of: providing a first solution, providing a second solution, and pouring the first solution into the second solution to be stirred at 400-600 rpm for 5-10 min to obtain the gliclazide nanosphere, wherein the first solution includes a solute having a gliclazide and an acrylic resin, and a solvent having an acetone and a methanol, and the second solution having a polyvinyl alcohol and a water.

Preferably, the first solution has a weight to volume ratio of the solute to the solvent ranged from 10/1 mg/ml to 180/5 mg/ml, and the polyvinyl alcohol has a weight-volume percentage ranged from 0.5 to 1.0%.

Preferably, the solvent has a volume ratio of the acetone to the methanol ranged from 1:1 to 5:1.

Preferably, the solute has a weight ratio of the gliclazide to the acrylic resin ranged from 1:1 to 1:10.

Preferably, the solvent has a volume ratio of the acetone to the methanol ranged from 1:1 to 5:1.

Preferably, the solute has a weight ratio of the gliclazide to the acrylic resin ranged from 1:1 to 1:10.

Preferably, the method further includes steps of: carrying out a first centrifugation after being stirred, washing the gliclazide nanosphere with water after the first centrifugation, and carrying out a second centrifugation.

Preferably, one of the centrifugations is carried out at 14,000-20,000 rpm for 10-15 minutes.

Preferably, the method further includes a step of freeze-drying the gliclazide nanosphere.

In accordance with further aspect of the present invention, a gliclazide nanosphere prepared by a manufacturing method mentioned is provided.

Preferably the gliclazide nanospheres have an average particle size ranged from 56.30 nm to 60.46 nm.

In accordance with the other aspect of the present invention, a high gliclazide concentration solution is provided. The solution includes a gliclazide nanosphere as mentioned.

In accordance with the other aspect of the present invention, a pharmaceutical composition is provided. The composition includes a pharmaceutically acceptable carrier and a pharmaceutically effective gliclazide nanosphere as mentioned.

Preferably, the composition is in a form selected from a group consisting of a capsule, a pastille, and a liposome.

The above aspects and advantages of the present invention will become more readily apparent to those ordinarily skilled in the art after reviewing the following detailed descriptions and accompanying drawings, in which:

DETAILED DESCRIPTION OF THE PREFERRED EMBODIMENT

Figure 1:
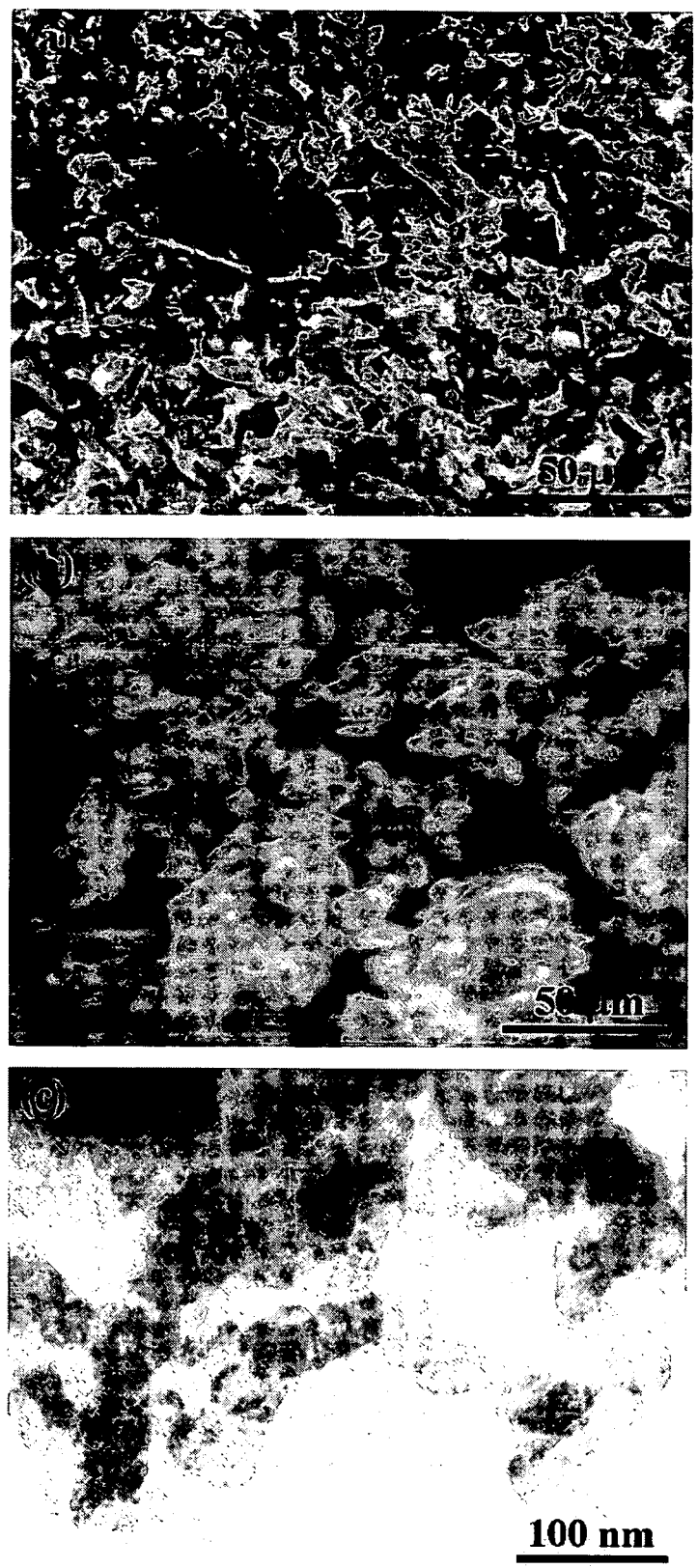
FIG. 1(a) shows the SEM image of GL pure drug at 350 times of amplification.
FIG. 1(b) shows the SEM image of GL solid complexes according to the prior art at 350 times of amplification.
FIG. 1(c) shows TEM image of GL nanospheres according to a preferred embodiment of the present application at 40,000 times of amplification.

The present invention will now be described more specifically with reference to the following embodiments. It is to be noted that the following descriptions of preferred embodiments of this invention are presented herein for the purposes of illustration and description only; it is not intended to be exhaustive or to be limited to the precise form disclosed.

Materials

Gliclazide was given from Lotus Pharmaceutical Co., Ltd. (Taipei, Taiwan). β-CD was purchased from Roquette Frères (Lestrem, France). Eudragit® E100 was obtained from Röhm GmbH & Co. KG (Darmstadt, Germany). Tolbutamide and Polyvinyl alcohol were purchased from Sigma Chemical Co. (Louis, USA). All the other materials purchased were of either reagent or analytical grade.

Preparation of Traditional GL Solid Complex

The traditional GL solid complex is prepared according to the prior art, which is summarized hereafter. Mainly, solid GL is weighed and poured into 50 ml of 1 N sodium hydroxide solution, and then β-CD is added and stirred until a clear solution is obtained therefrom. 50 ml of 1 N hydrochloric acid is dripped into the solution and stirred for 2 hours. The formed precipitate is separated by vacuum filtration and washed repeatedly for three times by cool alcohol and then dried at room temperature.

Preparation of GL Nanospheres

The GL nanosphere according to a first embodiment of the present invention is prepared by a precipitation-solvent evaporation method. 10 mg of GL and 100 mg Eudragit® E100 (registered trademark) are dissolved entirely in a mixture of acetone (2 ml) and methanol (1 ml). The solution is poured into 25 ml of polyvinyl alcohol aqueous solution (1.0%, w/v) and stirred at 400-600 rpm for 5-10 min. The mixing solution was then centrifuged (14,000-20,000 rpm for 10-15 min; St Herblain, France), washed and redispersed in the distilled water. After repeated three times of this procedure, the final dispersed GL nanospheres are dried using a freeze drying method.

Determination of Drug Loading

The following procedures are carried out for measuring and evaluating the respective loading efficiency of the above-prepared GL solid complexes and GL nanospheres. GL nanospheres and the solid GL complexes are respectively dissolved in distilled water to obtain a respective homogenous solution thereof. The amount of GL presented in GL nanospheres and the solid GL complexes are calculated from the following equations (1) and (2).

$$\text{Drug recovery (\%)} = \frac{\text{weight of drug in nanospheres/solid complex}}{\text{weight of drug loaded in the system}} \times 100 \quad (1)$$

$$\text{Drug content (\%)} = \frac{\text{weight of drug in nanospheres/solid complex}}{\text{weight of nanospheres/solid complex recovered}} \times 100 \quad (2)$$

The contents of GL in the respective GL nanospheres and the GL solid complexes were assayed using the HPLC method with Waters 2690D separations module (Milford, USA) and Supelco Discovery® (registered trademark) C18 column (5 μm, 250×4.6 mm I.D.) (Bellefonte, USA). The mobile phase consisted of methanol/water (65:35 v/v) adjusted to pH 3.0 with phosphoric acid at the flow rate of 1.0 ml/min. A 20 μl of sample, i.e. GL nanospheres or the GL solid complexes, and tolbutamide as internal standard were injected together and absorbed at 225 nm with Waters 2996 photodiode array detector. The standard fresh GL solutions for preparation of calibration curve was measured at 8:00 am, 10:00 am, 12:00 pm, 2:00 pm, 4:00 pm and 6:00 pm for six consecutive days. The average, standard deviation, variation and relative difference of GL contents in either GL nanospheres or the GL solid complexes were calculated to evaluate the stability of analytic condition, as well as the precision and the recurrence of measured data.

Particle Size Measurement

The average particle size of GL nanoparticles, GL solid complexes, the β-CD and the gliclazide pure drug were measured by the method of photon correlation spectroscopy (PCS) using Malvern Zetasizer 3000HSA (Malvern Worcestershire, UK). Prior to measurements, about 50 mg of each sample were diluted with 100 ml of ethylene glycol. The sizes of the above-mentioned four particle distributions were estimated by setting the intensity of the scattered light at λ=750 nm and the scattering angle at θ=90°. The background medium, i.e. the ethylene glycol (η=16.1 mPa·s) with the refractive index thereof being 1.431.

Morphological Analysis of Particles

The morphology of the solid complex and GL pure drug are observed using a 10 Jeol JSM 5300 SEM (Tokyo, Japan). A little amount of these two samples are placed in turn on a copper support with an adhesive carbon foil. The samples are then coated with gold at 10 mA for 3 min by Jeol JEC-1100E ion sputter (Tokyo, Japan) and observed at 10 kV. 0.6 μl of GL nanospheres solution containing 0.01% of phosphotungstic acid is deposited on a transmission electron microscope (TEM) copper grid coated with a carbon film and then dried at 25° C. GL nanospheres are observed at 100 kV with a JEM-2000 EX II (Tokyo, Japan).

Please refer to Table 1, which shows the precision and accuracy of the chromatography assay for determining the drug loading of the present application. As show in Table 1, the calibration curve of GL, Y=0.0198X-0.0079 (r=0.9999), has showed an excellent linear relationship with concentration range between 10.0 and 100.0 μg/ml. In addition, the lowest measurable concentration was 10.0 μg/ml with a C.V. % ranged from 0.31 to 3.50.

TABLE 1

Intra-day and Inter-day analytical precision and accuracy of GL determination

| | Intra-day (n = 6) | | | Inter-day (n = 6) | |
|---|---|---|---|---|---|
| Concentration (μg/ml) | Precision Mean ± S.D. (C.V. %) | Accuracy R.E. (%) | | Precision Mean ± S.D. (C.V. %) | Accuracy R.E. (%) |
| 10.00 | 9.97 ± 0.32 (3.21) | −0.30 | | 10.01 ± 0.35 (3.50) | 0.10 |
| 20.00 | 19.95 ± 0.29 (1.45) | −0.25 | | 20.12 ± 0.48 (2.39) | 0.60 |
| 40.00 | 40.19 ± 0.23 (0.57) | 0.48 | | 39.89 ± 0.36 (0.90) | −0.28 |
| 80.00 | 80.09 ± 0.35 (0.44) | 0.11 | | 81.03 ± 0.29 (0.36) | 1.29 |
| 100.00 | 100.28 ± 0.31 (0.31) | 0.28 | | 99.98 ± 0.32 (0.32) | −0.02 |

DSC Thermogram Studies

The differential scanning calorimetry, DSC, scans of GL pure drug, GL solid complex and GL nanospheres are recorded on a Perkin-Elmer model DSC 7 (Norwalk, USA). The instrument is calibrated with indium and zinc prior to analyzing the samples under nitrogen at the flow rate of 20 ml/min. 4 mg of each sample mentioned are scanned in sealed aluminum pans at the heating rate of 20° C./min over the temperature range of 50~200° C.

FTIR Spectroscopic Studies

The Fourier Transform Infrared spectrometry, FTIR, spectra were performed on Perkin-Elmer Spectrum System 2000 FTIR spectrometer (Norwalk, USA). GL pure drug, GL solid complexes and GL nanospheres for this assay are further prepared by the KBr disc method and scanned at resolution of 4 cm$^{-1}$ over the wavenumber region 4000~400 cm$^{-1}$. Air was used as the background and the data were averaged from 10 scans.

Dissolution Test

According to the USP 24 paddle apparatus, in vitro dissolution tests are performed with Hanson SR8 Plus (Chatsworth, USA). Three samples containing 80 mg of GL pure drug, GL solid complexes with an equivalent amount of GLs and GL nanospheres with an equivalent amount of GLs are poured separately into 900 ml deionized water at 37±0.5° C. with stirring rate at 100 rpm. Afterwards, 0.2 ml of each sample was withdrawn respectively at 1, 3, 5, 10, 15, 30, 60 and 120 min by the Waters transfer module (Milford, USA). Subsequently, the concentration of the samples was assayed using the HPLC method. The dissolution profiles are evaluated by the dissolution efficiency (DE) parameter (Khan, 1975) and the dissolved percentage (DP). The DE of GL pure drug, GL nanospheres and GL solid complex are calculated from the following equation (3).

$$\text{Dissolution efficiency}(DE) = \frac{\int_{t_1}^{t_2} y \cdot dt}{y_{100} \cdot (t_2 - t_1)} \times 100\% \quad (3)$$

wherein, y represents the percentage of dissolved product;
t1 and t2 represents the two different time points
y100 represents the maximum percentage of the dissolved sample Please refer to the Table 2, which shows the respective GL encapsulation efficiencies of GL solid complexes and GL nanospheres. The loading efficiencies of GL solid complex and GL nanospheres are calculated from the mentioned equations (1) and (2). As shown in Table 2, between the loading efficiencies of GL solid complex (60.50±1.42%) and GL nanospheres (56.86±2.06%), there is no obvious differences. Consequently, GL nanospheres according to the preferred embodiment of the present application could provide a GL loading efficiency similar to that of traditional GL solid complexes.

TABLE 2

GL encapsulation efficiencies of GL solid complexes and GL nanospheres (n = 10)

| Materials | Loading Amount (%) |
|---|---|
| Solid complex | 60.50 ± 1.42 |
| Nanospheres | 56.86 ± 2.06 |

Please refer to the Table 3, which shows the respective mean particle size of GL pure drug, the β-CD, GL solid complexes and GL nanospheres. The mean particle size of β-CD was 161.03±3.12 μm, however the mean particle size of GL solid complex was 68.29±2.76 μm (prepared from the neutralization method as mentioned in the above contexts). Because of the hydrogen bonding therein, the molecules of β-CD are bonded together and formed the bigger particles than those in GL solid complexes. In addition, the mean particle size of GL nanospheres (58.38±2.08 nm) is one thousands times smaller than that of GL solid complexes. Thereby, it demonstrates that GL nanospheres had a bigger outer particle surface in compare to that of GL solid complexes under the same amount of encapsulated GL drug.

TABLE 3

Mean particle size of GL pure drug, β-CD, GL solid complexes and GL nanospheres (n = 3)

| Materials | Mean size ± S.D. |
|---|---|
| GL | 47.56 ± 2.11 μm |
| β-CD | 161.03 ± 3.12 μm |

TABLE 3-continued

Mean particle size of GL pure drug, β-CD, GL solid complexes and GL nanospheres (n = 3)

| Materials | Mean size ± S.D. |
|---|---|
| Solid complex | 68.29 ± 2.76 μm |
| Nanospheres | 58.38 ± 2.08 nm |

Please refer to FIGS. 1(a)~1(c), which are respectively the morphology photos of GL pure drug, GL solid complexes and GL nanospheres. The scanning electron microscopy (SEM) is used to observe the shape of particle. As shown in FIG. 1(a), the SEM image of GL pure drug shows many irregular flakes revealing its crystal character. As shown in FIG. 1(b), the SEM image of GL solid complex indicates that many masses gathered together and lost the crystal character shown in GL pure drug. The transmission electron microscopy (TEM) was utilized to examine the internal formation of GL nanospheres. As shown in FIG. 1(c), the TEM image of GL nanospheres has no crystal character as shown in GL pure drug. The particles of GL nanospheres are rather shown as a homogeneous matrix without any sign of a phase separation usually presented between the pure drug and the polymer therefor.

Figure 2:
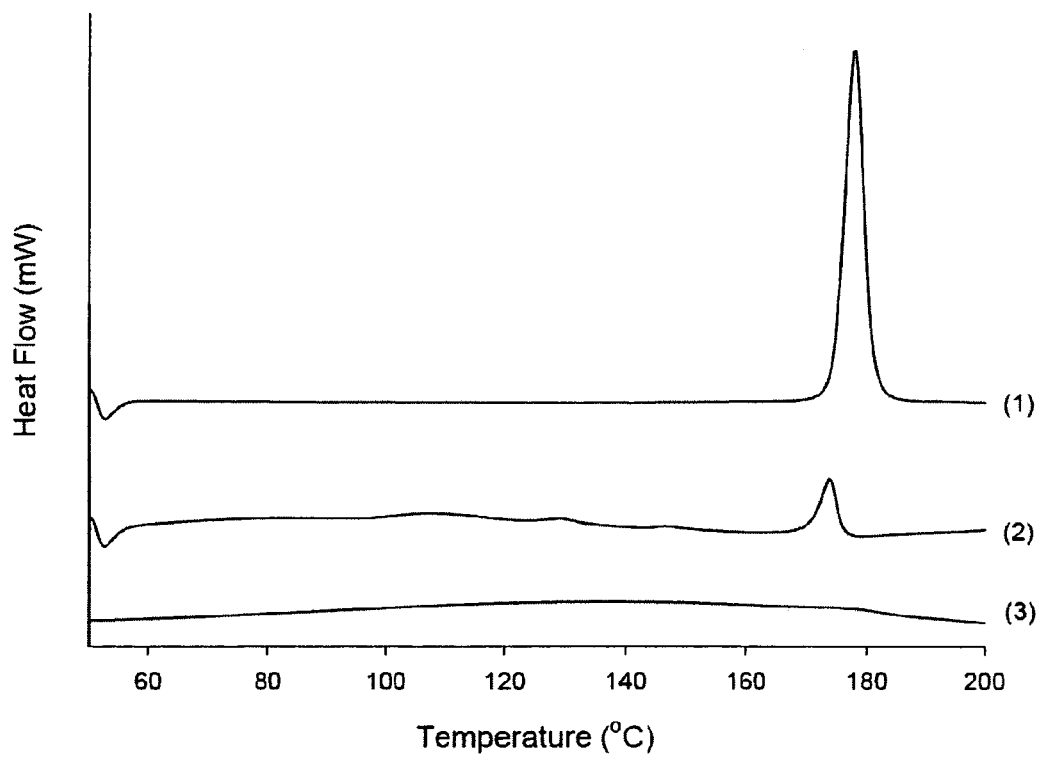
FIG. 2 shows the DSC curves of GL pure drug, GL solid complexes, and GL nanospheres.

DSC thermogram study is known as a fast and relatively inexpensive technique to examine the absence of the drug melting endotherm and to verify if the drug is successfully complexed or completely dispersed into the polymeric matrix. Please refer to the FIG. 2, which shows the results of DSC thermogram for GL pure drug, GL solid complexes and GL nanospheres. The DSC curve of GL pure drug shows an endothermic event of a melting peak with the onset temperature of 175° C. From the thermogram, it is found that the GL solid complexes and GL nanospheres have obvious different reactions. The GL solid complexes prepared from neutralization according to the prior art showed a very small melting peak at temperature of 175° C., which may be caused by the remaining GLs therein. This also indicates that most of GL molecules are dispersed into the β-CD cavities and their recrystallizations are almost restrained. The thermal behavior of GL nanospheres demonstrates no reaction from any temperature intervals. This occurrence could be attributed to that the molecules of GL are successfully dispersed into the polymeric matrix according to the preferred embodiment of the present application.

Figure 3:
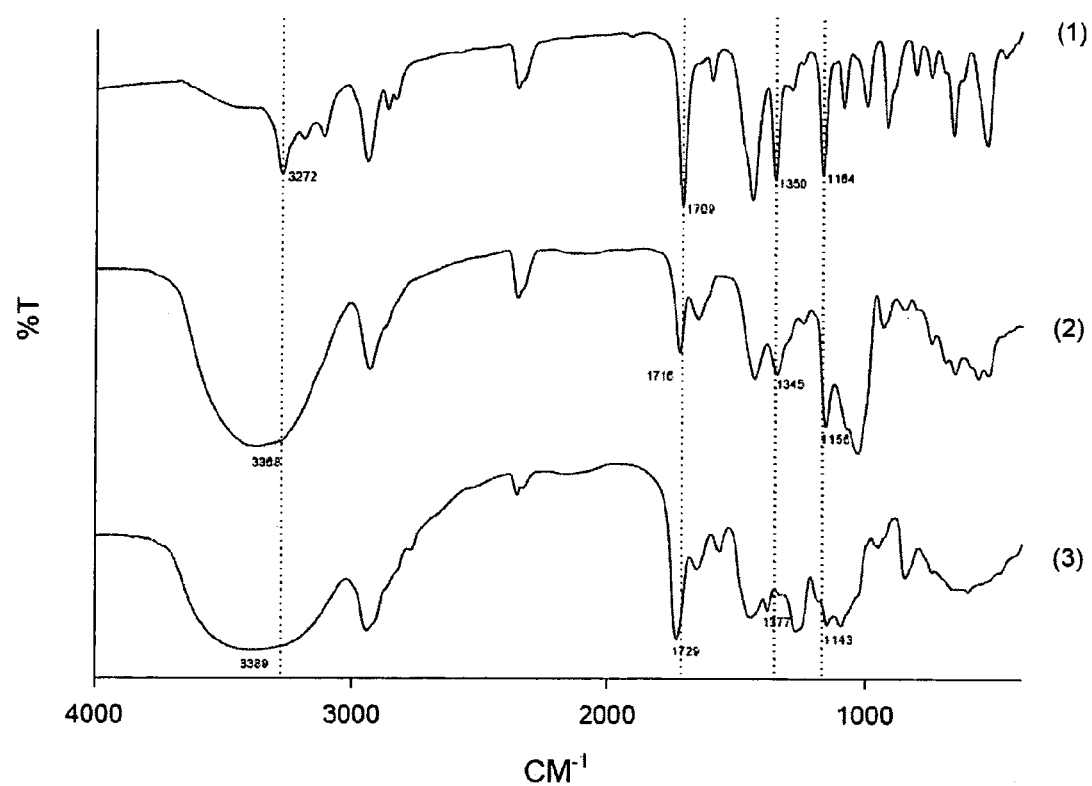
FIG. 3 shows the FTIR spectra of GL pure drug, GL solid complexes, and GL nanospheres.

Please refer to FIG. 3 and Table 4, for showing the FTIR spectra of GL pure drug (1), GL solid complexes (2) and GL nanospheres (3). The FTIR spectra are employed to confirm the complexation of GL/β-CD from neutralization according to the prior art and the dispersion of GL in polymeric matrix of nanospheres according to the present application. According to the mentioned analysis, the spectrum of GL pure drug (1) for carbonyl group showed a sharp concave curve at 1709 $cm^{-1}$. The band of GL solid complex (2), however, was broader with less frequency and shifted from 1709 to 1716 $cm^{-1}$. This reaction seems to result from the interaction between the hydroxyl groups of β-CD and the carbonyl groups of GL that is in good agreement with the published researches. The band of GL nanospheres (3) was similar to that of GL solid complexes (2), which is also a broader band with less frequency, and shifted from 1709 to 1729 $cm^{-1}$. This phenomenon suggested that Eudragit® E100 has interacted with GL.

Please only refer to Table 4 which is a comparison table for FTIR spectra of GL pure drug (1), GL solid complexes (2) and GL nanospheres (3). For the sulphonyl group bands, the spectra of GL pure drug (1) are characterized by a symmetric stretching peak at 1164 $cm^{-1}$ and an antisymmetric stretching peak at 1350 $cm^{-1}$. The symmetric vibration peak of the GL solid complexes (2) appears less frequency and shifts from 1164 to 1156 $cm^{-1}$, whereas the antisymmetric vibration peak thereof performs the same frequency reduction and shifts from 1350 to 1345 $cm^{-1}$. Based on the previous reports, the reasons for this phenomenon might be the interaction between the oxygen atoms of GL and the hydrogen atoms of β-CD of the traditional GL solid complexes. The symmetric vibration peak of GL nanospheres (3) according to the present application also has less frequency in comparison with GL pure drug (1) and shifts from 1164 to 1143 $cm^{-1}$; however, unlike the GL complexes, the antisymmetric vibration peak of GL nanospheres (3) appears more frequency and shifts from 1350 to 1377 $cm^{-1}$. It is supposed that the interaction between GL and Eudragit® E100 in GL nanospheres causes this reaction.

TABLE 4

Comparison of FTIR spectra from GL pure drug, GL solid complexes and GL nanospheres (n = 10)

| GL ($cm^{-1}$) | Solid complex ($cm^{-1}$) | Nanospheres ($cm^{-1}$) | Comment |
|---|---|---|---|
| 1164 | 1156 | 1143 | Change in S=O symmetric stretching |
| 1350 | 1345 | 1377 | Change in S=O antisymmetric stretching |
| 1709 | 1716 | 1729 | Change in C=O stretching |
| 3272 | 3368 | 3389 | Change in N—H stretching |

Further, for the amino group, GL pure drug (1) demonstrates an evident peak at 3272 $cm^{-1}$. Nevertheless, a slight curve shifting from 3272 to 3368 $cm^{-1}$ appears on the inclusion complex band, i.e. the band for GL solid complexes (2). This phenomenon corresponds with the previous reports as well. In addition, the band of GL nanospheres (3) presents the similar upward movement as shown in the band for GL solid complexes (2), and has a peak shifts from 3272 to 3389 $cm^{-1}$. The reason of this phenomenon may be attributed from the interaction between GL and Eudragit® E100 in GL nanospheres. In short, the GL solid complex prepared from neutralization according to the prior art has no significant characters of GL pure drug in FTIR spectrum, suggesting that the complex is well formed. Besides, the GL nanospheres according to the present application from FTIR spectrum analysis shows no significant character of GL pure drug and suggests that the molecules of GL disperses completely into its polymeric matrix.

Dissolution Behavior

Figure 4:
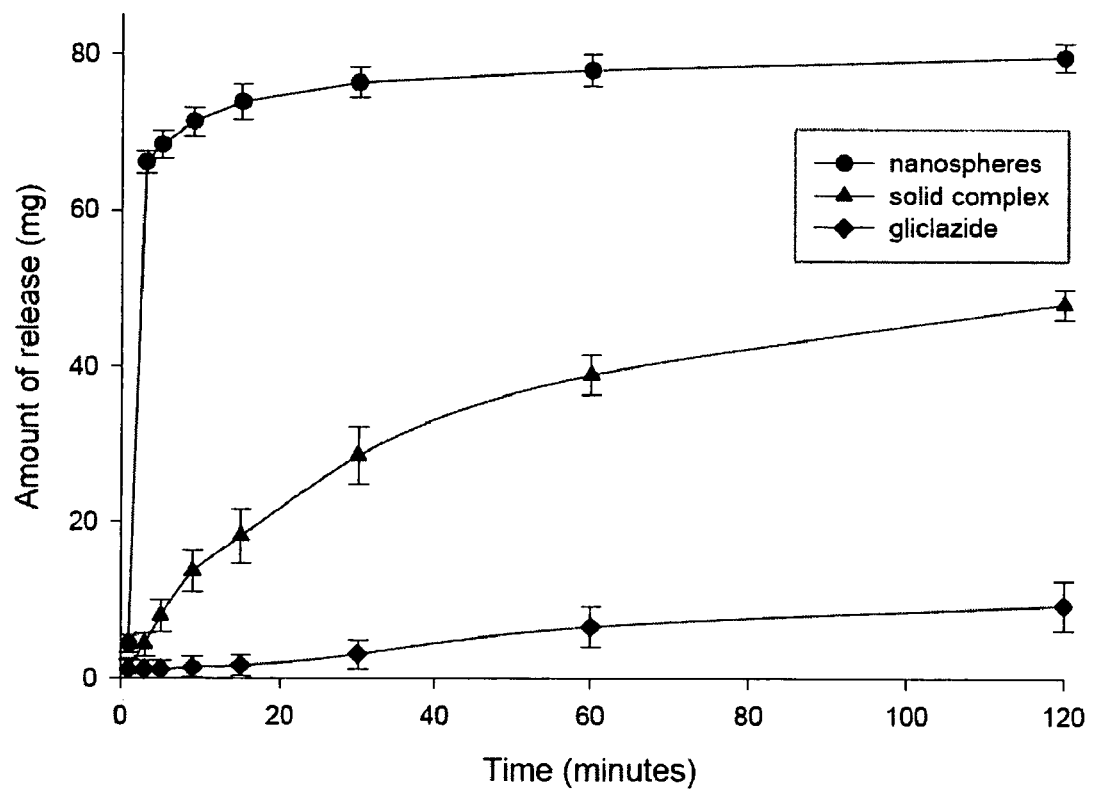
FIG. 4 shows the dissolution profile of GL pure drug, GL solid complexes, and GL nanospheres.

Please refer to FIG. 4 and Table 5, which are the dissolution curve and comparison table thereof for GL pure drug (diamond), GL solid complexes (triangle) and GL nanospheres (dot). It is shown that the dissolution rate for the GL nanospheres (dot) is greater than GL solid complexes (diamond) and GL pure drug (diamond).

TABLE 5

Comparison of the D.E. and D.P. from GL pure drug, GL solid complexes and GL nanospheres (n = 6)

| | 5 min. | | 30 min. | | 60 min. | |
|---|---|---|---|---|---|---|
| Materials | $DE_5$ | $DP_5$ | $DE_{30}$ | $DP_{30}$ | $DE_{60}$ | $DP_{60}$ |
| GL | 0.0129 | 1.44 | 0.0229 | 3.84 | 0.0416 | 8.23 |
| Solid complex | 0.0463 | 5.44 | 0.2119 | 35.67 | 0.3165 | 48.54 |
| Nanospheres | 0.5180 | 82.66 | 0.8533 | 95.34 | 0.9081 | 97.25 |

From Table 5, it is cleared that the DP for GL pure drug is 1.44%, while DE for GL solid complex and GL nanospheres are 5.44% 82.66% respectively after five minutes. Even after 60 minutes, the DPs for GL pure drug and for GL solid complexes are only 8.23% and 48.54% respectively. This result indicated that GL nanospheres according to the present application have superior drug release percentage in a very short period in comparison with GL pure drug and transitional GL solid complexes. Moreover, the DEs of GL pure drug are 0.0129 at five minutes and 0.0416 at 60 minutes. The DE for GL solid complex has a better performance at five minutes (0.0463) and at 60 minutes (0.3165) than GL pure drug. Nevertheless, the DE for GL nanospheres has the highest dissolution efficiencies 0.5180 at five minutes and 0.9081 at 60 minutes.

From both results of DP and DE of the mentioned three samples, it is found that GL nanosphere has a greater performance of dissolution profiles than GL solid complex and GL pure drug. Although the exterior of cyclodextrin is hydrophilic, it has limited effect on increasing the dissolution rate of GL inclusion complex, i.e. the GL solid complex (2) which formed a slow upward curve as shown in FIG. 4. This might be due to the hydrogen bonding of β-CD, causing the particles aggregation of GL inclusion complex, i.e. the GL solid complex and the decrease of the dissolution rate. This finding is very important and indicates that GL nanosphere prepared according to the method disclosed in the present application provides a higher performance on the dissolution rate and solubility than the GL solid complexes prepared by the complexation method according to the prior art.

Based on the above, the present application provides a gliclazide nanosphere, a manufacturing method therefor and an application thereof, where the dissolution profiles, and the whole particle surface thereof are increased, the drug wettability is enhanced, and the undesired aggregation and side effects caused from β-CD are prevented. Furthermore, the present invention is good for providing an immediate released dosage for GL. Accordingly, the present invention not only overcomes the foregoing disadvantages of the conventional GL, but also has lots of mentioned advantages. Hence, the present application useful for the clinical therapy.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A manufacturing method for a gliclazide nanosphere, comprising steps of:
    providing a first solution comprising:
        a solute having a gliclazide and an acrylic resin; and
        a solvent having an acetone and a methanol;
    providing a second solution having a polyvinyl alcohol and a water;
    pouring the first solution into the second solution to be stirred at 400-600 rpm for 5-10 min to obtain the gliclazide nanosphere.

2. A method as claimed in claim 1, wherein the first solution has a weight to volume ratio of the solute to the solvent ranged from 10/1 mg/ml to 180/5 mg/ml, and the polyvinyl alcohol has a weight-volume percentage ranged from 0.5 to 1.0%.

3. A method as claimed in claim 2, wherein the solvent has a volume ratio of the acetone to the methanol ranged from 1:1 to 5:1.

4. A method as claimed in claim 2, wherein the solute has a weight ratio of the gliclazide to the acrylic resin ranged from 1:1 to 1:10.

5. A method as claimed in claim 1, wherein the solvent has a volume ratio of the acetone to the methanol ranged from 1:1 to 5:1.

6. A method as claimed in claim 1, wherein the solute has a weight ratio of the gliclazide to the acrylic resin ranged from 1:1 to 1:10.

7. A method as claimed in claim 1, further comprising steps of:
    carrying out a first centrifugation after being stirred;
    washing the gliclazide nanosphere with water after the first centrifugation; and
    carrying out a second centrifugation.

8. A method as claimed in claim 7, wherein one of the centrifugations is carried out at 14,000-20,000 rpm for 10-15 minutes.

9. A method as claimed in the claim 1, further comprising a step of:
    freeze-drying the gliclazide nanosphere.

* * * * *

UNITED STATES PATENT AND TRADEMARK OFFICE
CERTIFICATE OF CORRECTION

PATENT NO. : 7,901,712 B2
APPLICATION NO. : 11/595250
DATED : March 8, 2011
INVENTOR(S) : Yung-Kuang Lo and Thau-Ming Cham Page 1 of 1

It is certified that error appears in the above-identified patent and that said Letters Patent is hereby corrected as shown below:

Title page, item [73] should read as follows:

Assignee: Kaohsiung Medical University
Kaohsiung (TW)

Signed and Sealed this
Seventh Day of August, 2012

David J. Kappos
*Director of the United States Patent and Trademark Office*